US012781261B2

(12) United States Patent
Lee et al.

(10) Patent No.: US 12,781,261 B2
(45) **Date of Patent: *Nov. 3, 2026**

(54) BIOLOGICAL SAMPLE PREPARATION AND REVERSE CROSSLINK TREATMENT BUFFER FOR MOLECULAR DIAGNOSTIC APPLICATIONS AND METHODS OF PRODUCTION AND USE THEREOF

(71) Applicant: Siemens Healthcare Diagnostics Inc., Tarrytown, NY (US)

(72) Inventors: Alex Hofai Lee, Fremont, CA (US); Jocelyn Lee, Castro Valley, CA (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 729 days.

This patent is subject to a terminal disclaimer.

(21) Appl. No.: 17/995,366

(22) PCT Filed: Apr. 20, 2021

(86) PCT No.: PCT/US2021/070426
§ 371 (c)(1),
(2) Date: Oct. 3, 2022

(87) PCT Pub. No.: WO2021/217172
PCT Pub. Date: Oct. 28, 2021

(65) Prior Publication Data

US 2023/0159987 A1 May 25, 2023

Related U.S. Application Data

(60) Provisional application No. 63/013,650, filed on Apr. 22, 2020.

(51) Int. Cl.
*C12Q 1/6806* (2018.01)

(52) U.S. Cl.
CPC .................................. *C12Q 1/6806* (2013.01)

(58) Field of Classification Search
USPC .......................................................... 536/25.4
See application file for complete search history.

(56) References Cited

U.S. PATENT DOCUMENTS

| | | | | |
|---|---|---|---|---|
| 8,530,228 | B2 | 9/2013 | Han et al. | |
| 9,771,571 | B2 | 9/2017 | Jensen et al. | |
| 10,233,440 | B2 | 3/2019 | Lai et al. | |
| 12,674,157 | B2 * | 7/2026 | Lee | C12N 1/06 |
| 2009/0312285 | A1 * | 12/2009 | Fischer | C12Q 1/6806 435/5 |
| 2013/0122496 | A1 * | 5/2013 | Haydock | C12Q 1/6806 435/6.12 |
| 2014/0275510 | A1 * | 9/2014 | Gundling | C12Q 1/6806 252/189 |
| 2016/0348153 | A1 * | 12/2016 | Narayanan | C12N 1/06 |

FOREIGN PATENT DOCUMENTS

| | | |
|---|---|---|
| EP | 1584923 | 10/2005 |
| WO | 9402645 | 2/1994 |

OTHER PUBLICATIONS

International Search Report for PCT/US2021/070426 dated Jul. 16, 2021.

Ingram "Mechanism of lysis of *Escherichia coli* by ethanol and other chaotropic agents." Journal of Bacteriology; vol. 146; No. 1; pp. 331-336;(1981).

"Formaldehyde and Cancer Risk"; (National Cancer Institute) Jun. 10, 2011.

* cited by examiner

*Primary Examiner* — Heather Calamita

(57) ABSTRACT

A biological sample preparation and reverse crosslink treatment reagent is disclosed in which all molecular pre-analytical and sample preparation steps can be performed on the biological sample in the single reagent. Also disclosed are kits containing the treatment reagent and methods of producing and using the treatment reagent.

19 Claims, No Drawings

BIOLOGICAL SAMPLE PREPARATION AND REVERSE CROSSLINK TREATMENT BUFFER FOR MOLECULAR DIAGNOSTIC APPLICATIONS AND METHODS OF PRODUCTION AND USE THEREOF

CROSS-REFERENCE TO RELATED APPLICATIONS

This application is a 35 U.S.C. 371 national application of international application no. PCT/US2021/070426 filed 20 Apr. 2021, which claims priority of U.S. Provisional application No. 63/013,650 filed 22 Apr. 2020, the contents of which are fully incorporated herein by reference.

STATEMENT REGARDING FEDERALLY SPONSORED RESEARCH OR DEVELOPMENT

Not Applicable.

BACKGROUND

US cervical screening guidelines recommend high risk human papillomavirus (HR-HPV) testing after abnormal cytological results are obtained, as well as regular pap smear/HR-HPV co-testing of women 30 years and older. Specimen collection and storage prior to HR-HPV testing currently uses two major liquid-based cytology media: ThinPrep® PreservCyt® cytology media (Hologic Inc., Malborough, MA) and SurePath™ cytology media (Becton Dickinson, Sparks, MD). Most HPV assays have been validated using ThinPrep® PreservCyt® specimens and approved by the US Food and Drug Administration (FDA). However, specimens collected in SurePath™ cytology media have been considered a challenge for nucleic acid analysis (NAA), as SurePath™ medium contains formaldehyde; while formaldehyde fixes cells and provides advantages from a cytological perspective, formaldehyde introduces chemical modifications of proteins, DNA, and RNA by forming crosslinking between amines of proteins and nucleic acids. These modifications are known to compromise the accuracy of any NAA performed on specimens collected and stored in formaldehyde-containing media. In fact, recent results suggested that the DNA recovery for molecular testing was reduced by 1000-fold for cell-spiked samples, and introducing false-negative HBV results in clinical specimens has raised safety concerns.

Several methods have been developed and evaluated to reverse the crosslinks of formaldehyde-fixed nucleic acids and proteins in formaldehyde-containing preservative fluid. For example, currently used methods for reversing the modifications/cross-linkages caused by formaldehyde-containing transport media include treatment of formaldehyde-fixed samples with: (1) Proteinase K; (2) hydrazine or hydrazide-containing formaldehyde scavenging compounds; (3) higher salt content buffers; and/or (4) basic conditions with surfactant(s) (such as SDS) at higher incubation temperatures. However, these treatments are designed to occur in the Molecular Pre-Analytical workflow and thus involve sample treatments before the sample preparation process, thereby resulting in additional processing architectures and workflow designs. These procedures also require additional processing time and personnel to accomplish these tasks.

Therefore, there is a need in the art for new and improved treatment buffers that overcome the disadvantages and defects in the prior art. In particular, there is a need for treatment buffers in which both reverse crosslinking and sample preparation can occur without requiring any Molecular Pre-Analytical (MOPA) processes. Such treatment buffers would increase throughput, reduce the complexity of the architecture design, and simplify the process by incorporating multiple steps seamlessly into a single step. It is to such treatment buffers, as well as kits containing same and methods of producing and using same, that the present disclosure is directed.

DETAILED DESCRIPTION

Before explaining at least one embodiment of the present disclosure in detail by way of exemplary language and results, it is to be understood that the present disclosure is not limited in its application to the details of construction and the arrangement of the components set forth in the following description. The present disclosure is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the medical procedures and techniques of, surgery, anesthesia, wound healing, and infectious control described herein are those well-known and commonly used in the art. Standard techniques are used for infection diagnostic and therapeutic applications.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions, kits, and/or methods disclosed herein can be made and executed without undue experimentation in light of the present disclosure. While the compositions, kits, and/or methods have been described in terms of particular embodiments, it will be apparent to those of skill in the art that variations may be applied to the compositions, kits, and/or methods and in the steps or in the sequence of steps of the methods described herein without departing from the concept, spirit, and scope of the present disclosure. All such similar substitutions and modifications apparent to those skilled in the art are deemed to be within the spirit, scope, and concept of the present disclosure as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

The use of ordinal number terminology (i.e., "first," "second," "third," "fourth," etc.) is solely for the purpose of differentiating between two or more items and, unless explicitly stated otherwise, is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps. For example, a process, method, article, or apparatus that comprises a list of elements is not necessarily limited to only those elements but may include other elements not expressly listed or inherently present therein.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. The term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "sample" as used herein will be understood to include any type of biological sample that may be utilized in accordance with the present disclosure. In certain embodiments, the sample may be any fluidic sample and/or sample capable of being fluidic (e.g., a biological sample mixed with a fluidic substrate). Examples of biological samples that may be utilized include, but are not limited to, whole blood or any portion thereof (i.e., plasma or serum), saliva, sputum, cerebrospinal fluid (CSF), surgical drain fluid, skin, intestinal fluid, intraperitoneal fluid, cystic fluid, sweat, interstitial fluid, extracellular fluid, tears, mucus, bladder wash, urine, swabs (such as, but not limited to, vaginal, cervical, rectal, oral, throat, and nasopharyngeal swabs, and the like), semen, fecal, pleural fluid, nasopharyngeal fluid, tissue, combinations thereof, and the like. In particular (but non-limiting) examples, the biological sample may be urine, stool, sexually transmitted infection (STI) swabs, respiratory collections, and the like.

Certain non-limiting embodiments of the present disclosure are directed to a sample preparation and reverse crosslink treatment reagent. Both reverse crosslinking and sample preparation can occur in the treatment reagent without requiring any Molecular Pre-Analytical (MOPA) processes; as such, the treatment buffer increases the throughput, reduces the complexity of the architecture design, and simplifies the process by incorporating multiple steps seamlessly into a single step.

Certain non-limiting embodiments are directed to a sample preparation and reverse crosslink treatment reagent that includes a base buffer containing a chaotropic agent (such as, but not limited to, guanidine thiocyanate), a polysorbate, and PEG (polyethylene glycol).

Each component present in the sample preparation and reverse crosslink treatment reagent can be present at any concentration so long as the sample preparation and reverse crosslink treatment reagent can function as described herein. For example (but not by way of limitation), each component of the sample preparation and reverse crosslink treatment reagent may be present at a concentration independently selected from about 0.0001%, about 0.0005%, about 0.001%, about 0.005%, about 0.01%, about 0.05%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 55%, about 60%, about 65%, about 70%, about 75%, about 80%, about 85%, about 90%, about 95%, or higher. In addition, each component may be present at a concentration that is independently selected from a range of two of any of the above values (i.e., a range from about 0.1% to about 10%, about 1% to about 20%, 15% to about 50%, a range of from about 10% to about 60%, etc.).

In other non-limiting examples, each component of the sample preparation and reverse crosslink treatment reagent may be present at a molar concentration of about 0.0001 M, about 0.0005 M, 0.001M, about 0.005M, 0.01 mM, about 0.05 mM, about 0.1 mM, about 0.2 mM, about 0.3 mM, about 0.4 mM, about 0.5 mM, about 0.6 mM, about 0.7 mM, about 0.8 mM, about 0.9 mM, about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 125 mM, about 150 mM, about 175 mM, about 200 mM, about 225 mM, about 250 mM, about 275 mM, about 300 mM, about 325 mM, about 350 mM, about 375 mM, about 400 mM, about 425 mM, about 450 mM, about 475 mM, about 500 mM, about 525 mM, about 550 mM, about 575 mM, about 600 mM, about 625 mM, about 650 mM, about 657 mM, about 700 mM, about 725 mM, about 750 mM, about 775 mM, about 800 mM, about 825 mM, about 850 mM, about 875 mM, about 900 mM, about 925 mM, about 950 mM, about 975 mM, about 1 M, about 1.5 M, about 2 M, about 2.5 M, about 3 M, about 3.5 M, about 4 M, about 4.5 M, about 5 M, about 6 M, about 7 M, about 8 M, about 9 M, about 10 M, about 11 M, about 12 M, about 13 M, about 14 M, about 15 M, about 16 M, about 17 M, about 18 M, about 19 M, about 20 M, and higher. In addition, each component may be present at a molar concentration that falls within a range of two of the above values (i.e., a range from about 0.1 mM to about 25 mM, a range of from about 1 mM to about 100 mM, etc.).

Any chaotropic agents known in the art or otherwise contemplated herein may be utilized in accordance with the present disclosure, as long as the sample preparation and reverse crosslink treatment reagent formed therefrom is capable of fully functioning as described herein.

In particular (but non-limiting) embodiments, guanidine thiocyanate is utilized as the chaotropic agent of the sample preparation and reverse crosslink treatment reagent. Guanidine thiocyanate may be present at any concentration that allows the reagent to function as described herein. Certain non-limiting examples of guanidine thiocyanate concentrations that may be utilized in accordance with the present disclosure include about 1 M, about 2 M, about 3 M, about 4 M, about 5 M, about 6 M, about 7 M, about 8 M, about 9 M, about 10 M, and the like, as well as any range formed from two of the above values or from two values that each fall between two of the above values (i.e., a range of from about 1 M to about 10 M, a range of from about 2.3 M to about 7.7 M, etc.).

In a particular (but non-limiting) embodiment, the sample preparation and reverse crosslink treatment reagent contains guanidine thiocyanate as the chaotropic agent, and the guanidine thiocyanate is present in the reagent at a concentration of about 5 M.

Any polysorbates known in the art or otherwise contemplated herein may be utilized in accordance with the present disclosure. In particular (but non-limiting) embodiments, the polysorbate present in the sample preparation and reverse crosslink treatment reagent is Polysorbate-20.

The polysorbate may be present in the sample preparation and reverse crosslink treatment reagent at any concentration that allows the reagent to function as described herein. Certain non-limiting examples of polysorbate concentrations that may be utilized in accordance with the present disclosure include about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, and the like, as well as any range formed from two of the above values or from two values that each fall between two of the above values (i.e., a range of from about 0.1% to about 20%, a range of from about 0.25% to about 8.6%, etc.).

In certain particular (but non-limiting) embodiments, the polysorbate is present in the sample preparation and reverse crosslink treatment reagent at a concentration in a range of from about 1% to about 20%.

In a particular (but non-limiting) embodiment, the polysorbate is present in the sample preparation and reverse crosslink treatment reagent at a concentration of about 10%.

Any polyethylene glycols (PEGs) known in the art or otherwise contemplated herein may be utilized in accordance with the present disclosure. In particular (but non-limiting) embodiments, the PEG present in the sample preparation and reverse crosslink treatment reagent is PEG8000.

The PEG may be present in the sample preparation and reverse crosslink treatment reagent at any concentration that allows the reagent to function as described herein. Certain non-limiting examples of PEG concentrations that may be utilized in accordance with the present disclosure include about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, and the like, as well as any range formed from two of the above values or from two values that each fall between two of the above values (i.e., a range of from about 0.1% to about 10%, a range of from about 0.25% to about 8.6%, etc.).

In certain particular (but non-limiting) embodiments, the PEG is present in the sample preparation and reverse crosslink treatment reagent at a concentration in a range of from about 0.1% to about 10%.

In a particular (but non-limiting) embodiment, the PEG is present in the sample preparation and reverse crosslink treatment reagent at a concentration of about 1.5%.

Any base buffers known in the art or otherwise contemplated herein may be utilized in accordance with the present disclosure. In particular (but non-limiting) embodiments, the base buffer is Tris. In other particular (but non-limiting) embodiments, the base buffer is sodium acetate.

The base buffer may be present in the sample preparation and reverse crosslink treatment reagent at any concentration and at any pH that allows the reagent to function as described herein. Certain non-limiting examples of base buffer concentrations that may be utilized in accordance with the present disclosure include about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 125 mM, about 150 mM, about 175 mM, about 200 mM, about 225 mM, about 250 mM, about 275 mM, about 300 mM, about 325 mM, about 350 mM, about 375 mM, about 400 mM, about 425 mM, about 450 mM, about 475 mM, about 500 mM, and the like, as well as any range formed from two of the above values or from two values that each fall between two of the above values (i.e., a range of from about 1 mM to about 100 mM, a range of from about 16 mM to about 105 mM, etc.). Certain non-limiting examples of pH values that may be utilized in accordance with the present disclosure include about 1, about 2, about 3, about 4, about 5, about 6, about 7, about 8, about 9, about 10, about 11, about 12, and the like, as well as any range formed from two of the above values or from two values that each fall between two of the above values (i.e., a pH in a range of from about 4 to about 9, a pH in a range of from about 4.1 to about 9.5, a pH in a range of from about 4 to about 7, a pH in a range of from about 8 to about 10, a pH in a range of from about 4 to about 6.5, a pH in a range of from about 4.1 to about 6.5, a pH in a range of from about 8.5 to about 9.5, a pH in a range of from about 8.6 to about 9.5, etc.).

In a particular (but non-limiting) embodiment, the sample preparation and reverse crosslink treatment reagent includes Tris as a base buffer at a concentration in a range of from about 1 mM to about 20 mM (such as, but not limited to, about 10 mM) and a pH in a range of from about 8 to about 10 (such as, but not limited to, a range of from about 8.5 to about 9.5).

In a particular (but non-limiting) embodiment, the sample preparation and reverse crosslink treatment reagent includes sodium acetate (NaOAc) as a base buffer at a concentration in a range of from about 10 mM to about 200 mM (such as, but not limited to, about 100 mM) and a pH in a range of from about 4 to about 7 (such as, but not limited to, a range of from about 4 to about 6.5).

In particular (but non-limiting) embodiments, the sample preparation and reverse crosslink treatment reagents of the present disclosure may further include at least one anti-foaming agent. Any anti-foaming agents known in the art or otherwise contemplated herein may be utilized in accordance with the present disclosure. In particular (but non-limiting) embodiments, the anti-foaming agent is Antifoam-A (Sigma-Aldrich, St. Louis, MO), Antifoam 204, or another silicone-based product.

The anti-foaming agent may be present at any concentration that allows the transport medium to function as described herein. Certain non-limiting examples of anti-foaming agent concentrations that may be utilized in accordance with the present disclosure include about 0.001%, about 0.00125%, about 0.002%, about 0.0025%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 4%, about 5%, about 6%, about 7%, about 8%, about 9%, about 10%, and the like, as well as any range formed from two of the above values or from two values that each fall between two of the above values (i.e., a range of from about 0.001% to about 0.1%, a range of from about 0.01% to about 0.8%, a range of from about 0.005% to about 0.05%, etc.).

In particular (but non-limiting) embodiments, the sample preparation and reverse crosslink treatment reagents of the present disclosure may further include at least one protease. Any proteases known in the art or otherwise contemplated herein may be utilized in accordance with the present disclosure. In particular (but non-limiting) embodiments, the protease is Protease K.

Certain particular (but non-limiting) embodiments of the present disclosure are directed to a sample preparation and reverse crosslink treatment reagent that includes guanidine thiocyanate; Polysorbate-20; PEG8000; and Tris base buffer.

Certain particular (but non-limiting) embodiments of the present disclosure are directed to a sample preparation and reverse crosslink treatment reagent that includes guanidine thiocyanate at a concentration of about 5 M; Polysorbate-20 at a concentration in a range of from about 1% to about 20%; PEG8000 at a concentration in a range of from about 0.1% to about 10%; and a base buffer selected from Tris and sodium acetate. When the base buffer is Tris, Tris is present at a concentration in a range of from about 1 mM to about 20 mM; when the base buffer is sodium acetate, sodium acetate is present at a concentration in a range of from about 10 mM to about 200 mM.

Certain particular (but non-limiting embodiments of the present disclosure are directed to a sample preparation and reverse crosslink treatment reagent that includes guanidine thiocyanate at a concentration of about 5 M; Polysorbate-20 at a concentration of about 10%; PEG8000 at a concentration of about 1.5%; and Tris base buffer at a concentration of about 10 mM.

Certain particular (but non-limiting embodiments of the present disclosure are directed to a sample preparation and reverse crosslink treatment reagent that includes guanidine thiocyanate at a concentration of about 5 M; Polysorbate-20 at a concentration of about 10%; PEG8000 at a concentration of about 1.5%; and sodium acetate base buffer at a concentration of about 100 mM.

Certain non-limiting embodiments of the present disclosure are directed to a kit containing any of the sample preparation and reverse crosslink treatment reagents disclosed or otherwise contemplated herein. In addition, the kit may further contain one or more other component(s) or reagent(s) for performing biological sample collection(s) and/or molecular diagnostic application(s) in accordance with the present disclosure. For example (but not by way of limitation), the kit may further contain at least one specimen collection device, a specimen preservative fluid, a cytology media, etc.

The nature of these additional component(s)/reagent(s) will depend upon various factors such as (but not limited to) the types of biological samples, transport and storage conditions, and molecular diagnostic assay formats to be utilized, and identification thereof is well within the skill of one of ordinary skill in the art; therefore, no further description thereof is deemed necessary.

Also, the various components/reagents present in the kit may each be in separate containers/compartments, or various components/reagents can be combined in one or more containers/compartments, depending on the cross-reactivity and stability of the components/reagents. In addition, the kit may include a set of written instructions explaining how to use the kit. A kit of this nature can be used in any of the methods described or otherwise contemplated herein.

Certain non-limiting embodiments of the present disclosure are directed to a mixture that includes a biological sample disposed within any of the sample preparation and reverse crosslink treatment reagents disclosed or otherwise contemplated herein.

The biological sample may be any biological sample disclosed or otherwise contemplated herein that contains one or more DNA/RNA targets that need to be preserved for subsequent detection via nucleic acid assays. For example (but not by way of limitation), the biological sample may be selected from urine, stool, sexually transmitted infection (STI) swabs, respiratory collections, blood or any portion thereof, saliva, sputum, cerebrospinal fluid (CSF), surgical drain fluid, intestinal fluid, intraperitoneal fluid, cystic fluid, sweat, interstitial fluid, extracellular fluid, tears, mucus, bladder wash, urine, swabs (such as, but not limited to, vaginal, cervical, rectal, oral, throat, and nasopharyngeal swabs, and the like), semen, pleural fluid, nasopharyngeal fluid, tissue, and combinations thereof.

In certain particular (but non-limiting) embodiments, the biological sample is (or has been) disposed in a collection medium comprising formaldehyde.

Certain non-limiting embodiments of the present disclosure are directed to a method of using any of the sample preparation and reverse crosslink treatment reagents disclosed or otherwise contemplated herein. In the method, a biological sample is disposed in any of the sample preparation and reverse crosslink treatment reagents disclosed or otherwise contemplated herein to form a mixture.

In certain particular (but non-limiting) embodiments, the method further includes the step of incubating the mixture at a temperature in a range of from about 65° C. to about 110° C. for a period in a range of from about 30 seconds to about 10 minutes. For example (but not by way of limitation), incubating the mixture at a temperature in a range of from about 85° C. to about 95° C. for a period in a range of from about 30 seconds to about 10 minutes, or the mixture may be incubated at a temperature of about 90° C. for a period in a range of from about 1 minute to about 5 minutes.

The biological sample utilized in the method may be any biological sample disclosed or otherwise contemplated herein that contains one or more DNA/RNA targets that need to be preserved for subsequent detection via nucleic acid assays. For example (but not by way of limitation), the biological sample may be selected from urine, stool, sexually transmitted infection (STI) swabs, respiratory collections, blood or any portion thereof, saliva, sputum, cerebrospinal fluid (CSF), surgical drain fluid, intestinal fluid, intraperitoneal fluid, cystic fluid, sweat, interstitial fluid, extracellular fluid, tears, mucus, bladder wash, urine, swabs, semen, pleural fluid, nasopharyngeal fluid, tissue, and combinations thereof.

In certain particular (but non-limiting) embodiments, the biological sample is (or has been) disposed in a collection medium (i.e., specimen preservative fluid, a cytology media, etc.) comprising formaldehyde prior to interaction with the sample preparation and reverse crosslink treatment reagent.

In certain particular (but non-limiting) embodiments, the method further comprises the step of performing at least one nucleic acid analysis step on the mixture.

In a particular (but non-limiting) embodiment, all molecular pre-analytical and sample preparation steps performed on the biological sample prior to nucleic acid analysis are performed on the mixture containing the biological sample disposed in the sample preparation and reverse crosslink treatment reagent.

EXAMPLES

Examples are provided hereinbelow. However, the present disclosure is to be understood to not be limited in its application to the specific experimentation, results, and laboratory procedures disclosed herein after. Rather, the Examples are simply provided as one of various embodiments and are meant to be exemplary, not exhaustive.

The present disclosure involves the development of a single reagent that can be utilized for both sample preparation and reverse crosslinking processes, thereby combining Molecular Pre-Analytical (MOPA) processing and sample preparation in one single step and at the same time. The architecture design also benefits from the simplicity of the reagent and methods of the present disclosure, as no MOPA steps, no additional bottles, no additional reagents, and no changes to the workflow are needed for handling specimens that are collected in formaldehyde-containing media.

The sample preparation and reverse crosslink treatment reagent of the present disclosure is a REACH compliant (EU) buffer that greatly increases the throughput and decreases complexity of architecture design while simplifying the process by incorporating multiple steps seamlessly in one single step and in one single reagent.

Certain non-limiting embodiments of the sample preparation and reverse crosslink treatment reagents used in this Example are shown in Table 1 and include 5M guanidine thiocyanate as chaotropic salt, Polysorbate-20 (i.e., Tween 20), PEG8000 for surfactants, and sodium acetate or Tris base buffer. The chaotropic agent guanidine thiocyanate was found to be capable of serving a similar reverse crosslink function as 2-imidazolidone (which was reported by Gen-Probe in U.S. Pat. No. 9,771,571), and capable of performing a similar chemical reaction as urea-, hydrazine-, or hydrazide-catalyzed reverse reaction of amine-formaldehyde fixation.

This Example explored the use of a single buffer reagent for both reverse crosslinking and sample preparation (including lysis and nucleic acid binding). This approach not only eliminates the Molecular Pre-Analytical (MOPA) process for reverse crosslinkage of treated samples, but also increases the throughput, reduces the complexity of architecture design, and simplifies the process by incorporating multiple steps seamlessly in one single step in the sample preparation process with the use of a single reagent.

The reagent and reverse crosslinking reagents of the present disclosure allow a single step of sample preparation to accomplish reverse crosslinking, lysis, and binding all together in a single buffer within 2-5 minutes at 90° C.-110° C. In contrast, the Roche COBAS® system requires a 30-minute pre-treatment step in SurePath™ Preservative Fluid (SPPH, Becton Dickinson, Sparks, MD) plus sample preparation workflow in a 120° C. high temperature treatment step, followed by incubation with Protease K and 2-imidazolidone for 15 minutes at 90° C. The single reagent and methods of the present disclosure allow for both pre-analytic and sample preparation steps to be performed in the single reagent and thus merge two steps together to save time and reduce architecture complexity. The present disclosure is the first to combine MOPA and sample preparation in one step.

Some of the specimens tested with the single reagent formulations of Table 1 are shown in Table 2, along with the cytology media and storage conditions used with the specimens and the reaction conditions utilized to accomplish the single step reaction of the methods disclosed herein, which combines MOPA and sample preparation. The efficiency of the reagent and reverse crosslinking step using the treatment reagents of the present disclosure were studied using specimens containing multiple genotypes of CT/GC (*Chlamydia trachomatis/Neisseria gonorrhoeae*) or HPV (Human papillomavirus), wherein the specimens were stored in SurePath™ cytology media (Becton Dickinson, Sparks, MD) or ThinPrep® PreservCyt® cytology media (Hologic Inc., Malborough, MA), and using CT/GC or HPV PCR Ct (Cycle Threshold). The Ct values were compared from different times spent at 90° C. incubation for reverse crosslinkage, lysis, and binding in a single step. The results indicated that the treatment reagents of the present disclosure are able to obtain efficient levels of crosslinkage and lysis using a variety of specimens stored under a variety of storage conditions and for various lengths of storage periods.

Thus, in accordance with the present disclosure, there have been provided compositions, mixtures, and kits, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

TABLE 1

Formulations of Exemplary Treatment Reagents Produced in Accordance with the Present Disclosure

| Formulation: | 1 | 2 | 3 | 4 | 5 | 6 |
|---|---|---|---|---|---|---|
| Guanidine Thiocyanate | 5M | 5M | 5M | 5M | 5M | 5M |
| Buffer | 100 mM NaOAc | 100 mM NaOAc | 10 mM Tris | 100 mM NaOAc | 10 mM Tris | 10 mM Tris |
| Polysorbate-20 | 10% | 10% | 10% | 10% | 10% | 10% |
| PEG8000 | 1.5% | 1.5% | 1.5% | 1.5% | 1.5% | 1.5% |
| pH | 4.1 | 4.5 | 8.6 | 6.5 | 9.5 | 8.6 |
| Antifoam-A | 0% | 0% | 0% | 0% | 0% | 0.005% |
| Protease K | 0% | 0% | 0% | 0% | 0% | 0% |

| Formulation: | 7 | 8 | 9 | 10 | 11 |
|---|---|---|---|---|---|
| Guanidine Thiocyanate | 5M | 5M | 5M | 5M | 5M |
| Buffer | 10 mM Tris | 100 mM NaOAc | 10 mM Tris | 10 mM Tris | 10 mM Tris |
| Polysorbate-20 | 10% | 10% | 10% | 10% | 10% |
| PEG8000 | 1.5% | 1.5% | 1.5% | 1.5% | 1.5% |
| pH | 8.6 | 4.5 | 8.6 | 8.6 | 8.6 |
| Antifoam-A | 0.05% | 0% | 0% | 0.005% | 0.05% |
| Protease K | 0% | 0.0003% | 0.0003% | 0.0003% | 0.0003% |

TABLE 2

Various Specimens and Treatment Conditions Successfully Utilized with the Treatment Reagent Formulations of Table 1*

| Specimen | Specimen Storage Conditions Prior to Treatment | Formulation from Table 1 | Treatment Conditions |
|---|---|---|---|
| CT/GC Urine Specimen | 2-8° C. for 1 week | 3 | 90° C. for 2 minutes |
| CT/GC Swab specimen | 2-8° C. for 1 week | 3 | 90° C. for 2 minutes |
| CT/GC ThinPrep ® medium | 2-8° C. for 6 weeks | 3 | 90° C. for 2 minutes |
| CT/GC SurePath ™ medium | 2-8° C. for 2 weeks | 2, 3 | 90° C. for 2 minutes |
| CT/GC SurePath ™ medium | RT for 1-4 weeks | 2, 3 | 90° C. for 2, 4, 6 minutes |
| CT/GC SurePath ™ medium | 45° C. for 2 weeks | 2, 3 | 90° C. for 2 minutes |
| CT/GC SurePath ™ medium | Freeze thaw −20° C. x3 | 3 | 90° C. for 2 minutes |
| HPV SurePath ™ medium | RT for 1-4 weeks | 1-11 | 90° C. for 2, 3, 4, 5 minutes |
| HPV ThinPrep ® medium | RT for 1-4 weeks | 1-11 | 90° C. for 2, 3, 4, 5, 6 minutes |
| HPV SurePath ™ medium | 45° C. for >3 hours | 3 | 90° C. for 2-5 minutes |
| HPV SurePath ™ medium | Freeze thaw −20° C. x3 | 3 | 90° C. for 2-5 minutes |
| CT/GC SurePath ™ medium | 4° C. for 2 weeks | 2, 9 | 110° C. for 2, 4, 8, 20 minutes |
| CT/GC SurePath ™ medium | 45° C. for 2 weeks | 2, 9 | 110° C. for 2, 4 minutes |
| CT/GC SurePath ™ medium | RT for 2 weeks | 2, 9 | 110° C. for 2, 4 minutes |
| HPV SurePath ™ medium | RT for 1-4 weeks | 3 | 65° C. for 2 minutes |
| HPV ThinPrep ® medium | RT for 1-4 weeks | 3 | 65° C. for 2 minutes |

*Raw data can be found in priority application U.S. Ser. No. 63/013,650 (the entire contents of which are expressly incorporated herein by reference)

What is claimed is:

1. A method, comprising the steps of:

obtaining a biological sample removed from a subject and present in a fluid-based collection medium;

contacting the biological sample with a fluidic sample preparation and reverse crosslink treatment reagent to form a fluidic mixture in which the biological sample is disposed within the fluidic reagent, wherein the fluidic reagent comprises guanidine thiocyanate, polysorbate, polyethylene glycol (PEG), and sodium acetate buffer having a pH in a range of from about 4 to about 6.5;

incubating the fluidic mixture at a temperature in a range of from about 65° C. to about 110° C. for a period in a range of from about 30 seconds to about five minutes, wherein the incubation step results in reverse cross-linkage, lysis, and nucleic acid binding; and performing at least one nucleic acid analysis step on the fluidic mixture.

2. The method of claim 1, wherein the polysorbate is polysorbate-20.

3. The method of claim 1, wherein the collection medium comprises formaldehyde.

4. The method of claim 1, wherein the collection medium is a cytology medium.

5. The method of claim 1, wherein prior to contact with the treatment reagent, the biological sample has been stored in the collection medium at storage conditions selected from: 2° C. to 8° C. for at least one week; room temperature for at least one week; and 45° for at least two weeks.

6. The method of claim 1, wherein the biological sample comprises a cervical swab, and wherein the nucleic acid analysis detects at least one sexually transmitted infection.

7. The method of claim 6, wherein the nucleic acid analysis detects HPV (human papillomavirus) or CT/GC (*Chlamydia trachomatis/Neisseria gonorrhoeae*).

8. The method of claim 1, wherein:

guanidine thiocyanate is present at a concentration of about 5 M;

polysorbate is polysorbate-20 present at a concentration in a range of from about 1% to about 20%; and PEG is PEG8000 present at a concentration in a range of from about 0.1% to about 10%.

9. The method of claim 8, wherein:

polysorbate-20 is present at a concentration of about 10%; and

PEG8000 is present at a concentration of about 1.5%.

10. A method, comprising the steps of:

obtaining a biological sample removed from a subject and present in a fluid-based collection medium;

contacting the biological sample with a fluidic sample preparation and reverse crosslink treatment reagent to form a fluidic mixture in which the biological sample is disposed within the fluidic reagent, wherein the fluidic reagent comprises guanidine thiocyanate, polysorbate, polyethylene glycol (PEG), and Tris buffer having a pH in a range of from about 8 to about 10;

incubating the fluidic mixture at a temperature in a range of from about 65° C. to about 110° C. for a period in a range of from about 30 seconds to about five minutes, wherein the incubation step results in reverse cross-linkage, lysis, and nucleic acid binding; and performing at least one nucleic acid analysis step on the fluidic mixture.

11. The method of claim 10, wherein the polysorbate is polysorbate-20.

12. The method of claim 10, wherein the collection medium comprises formaldehyde.

13. The method of claim 10, wherein the collection medium is a cytology medium.

14. The method of claim 10, wherein prior to contact with the treatment reagent, the biological sample has been stored in the collection medium at storage conditions selected from: 2° C. to 8° C. for at least one week; room temperature for at least one week; and 45° for at least two weeks.

15. The method of claim 10, wherein the biological sample comprises a cervical swab, and wherein the nucleic acid analysis detects at least one sexually transmitted infection.

16. The method of claim 15, wherein the nucleic acid analysis detects HPV (human papillomavirus) or CT/GC (*Chlamydia trachomatis/Neisseria gonorrhoeae*).

17. The method of claim 10, wherein:

guanidine thiocyanate is present at a concentration of about 5 M;

polysorbate is polysorbate-20 present at a concentration in a range of from about 1% to about 20%; and PEG is PEG8000 present at a concentration in a range of from about 0.1% to about 10%.

18. The method of claim 17, wherein:

polysorbate-20 is present at a concentration of about 10%; and

PEG8000 is present at a concentration of about 1.5%.

19. A method, comprising the steps of:

obtaining a biological sample removed from a subject and present in a fluid-based collection medium;

contacting the biological sample with a fluidic sample preparation and reverse crosslink treatment reagent to form a fluidic mixture in which the biological sample is disposed within the fluidic reagent, wherein the fluidic reagent comprises:

guanidine thiocyanate present at a concentration of about 5 M;

polysorbate-20 present at a concentration in a range of from about 5% to about 20%;

polyethylene glycol (PEG) present at a concentration in a range of from about 0.1% to about 2.5%; and a base buffer selected from:

sodium acetate buffer present at a concentration in a range of from about 50 mM to about 200 mM and having a pH in a range of from about 4 to about 6.5; or Tris buffer present at a concentration in a range of from about 1 mM to about 20 mM and having a pH in a range of from about 8 to about 10;

incubating the fluidic mixture at a temperature in a range of from about 65° C. to about 110° C. for a period in a range of from about 30 seconds to about five minutes, wherein the incubation step results in reverse cross-linkage, lysis, and nucleic acid binding; and performing at least one nucleic acid analysis step on the fluidic mixture.

* * * * *